US00PP17781P2

(12) United States Plant Patent
Lamb et al.

(10) Patent No.: US PP17,781 P2
(45) Date of Patent: Jun. 5, 2007

(54) ***ANTHURIUM* PLANT NAMED 'TWYAN0015'**

(50) Latin Name: *Anthurium hybrida*
Varietal Denomination: TWYAN0015

(75) Inventors: Ann E. Lamb, Sebring, FL (US); Marianne E. Knauss, Longwood, FL (US)

(73) Assignee: Twyford International, Inc., Apapka, FL (US)

( * ) Notice: Subject to any disclaimer, the term of this patent is extended or adjusted under 35 U.S.C. 154(b) by 16 days.

(21) Appl. No.: 11/230,746

(22) Filed: Sep. 20, 2005

(51) Int. Cl.
*A01H 5/00* (2006.01)

(52) U.S. Cl. ..... Plt./365

(58) Field of Classification Search ..... Plt./365
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Anthurium* plant named 'TWYAN0015', characterized by its upright, outwardly arching and symmetrical plant form; compact growth habit; freely clumping habit; full, dense and bushy appearance; relatively small, glossy and dark green-colored leaves; freely flowering habit; inflorescences positioned at or slightly above foliar plane; and relatively small inflorescences with bright red-colored spathes and creamy white-colored spadices.

2 Drawing Sheets

Botanical designation: *Anthurium hybrida.*
Cultivar denomination: 'TWYAN0015'.

BACKGROUND OF THE INVENTION

The present Invention relates to a new and distinct cultivar of *Anthurium* plant, botanically known as *Anthurium hybrida* and hereinafter referred to by the name 'TWYAN0015'.

The new *Anthurium* is the result of a planned breeding program conducted by the Inventors in Apopka, Fla. The objective of the breeding program is to create new fast-growing *Anthurium* cultivars with freely clumping habit, dark green-colored leaves, red-colored spathes and resistance to pathogens.

The new *Anthurium* originated from a cross-pollination made by the Inventors on Oct. 27, 1999 of the *Anthurium hybrida* cultivar Cherry Red, disclosed in U.S. Plant Pat. No. 12,315, as the female, or seed, parent with the *Anthurium hybrida* cultivar Y-14, not patented, as the male, or pollen, parent. The new *Anthurium* was discovered and selected by the Inventors in August, 2002 as a single plant within the progeny of the stated cross-pollination in a controlled environment in Apopka, Fla. The new *Anthurium* was selected on the basis of its plant habit and attractive foliage and spathe coloration.

Asexual propagation of the new cultivar by tissue cultured since August, 2002 in a controlled environment in Apopka, Fla., has shown that the unique features of this new *Anthurium* are stable and reproduced true to type in successive generations.

SUMMARY OF THE INVENTION

The following traits have been repeatedly observed and are determined to be the unique characteristics of 'TWYAN0015'. These characteristics in combination distinguish 'TWYAN0015' as a new and distinct cultivar of *Anthurium:*

1. Upright, outwardly arching and symmetrical plant form.
2. Compact growth habit.
3. Freely clumping habit; full, dense and bushy appearance.
4. Relatively small, glossy and dark green-colored leaves.
5. Freely flowering habit.
6. Inflorescences positioned at or slightly above foliar plane.
7. Relatively small inflorescences with bright red-colored spathes and creamy white-colored spadices.

In side-by-side comparisons conducted by the Inventors in Apopka, Fla., plants of the new *Anthurium* differed from plants of the female parent, the cultivar Cherry Red, in the following characteristics:

1. Plants of the new *Anthurium* grew faster than plants of the cultivar Cherry Red.
2. Plants of the new *Anthurium* were more compact than plants of the cultivar Cherry Red.
3. Plants of the new *Anthurium* were more freely-branching than plants of the cultivar Cherry Red.
4. Plants of the new *Anthurium* had smaller leaves than plants of the cultivar Cherry Red.
5. Plants of the new *Anthurium* and the cultivar Cherry Red differed in leaf coloration.
6. Plants of the new *Anthurium* were more freely and earlier flowering than plants of the cultivar Cherry Red.
7. Inflorescences of plants of the new *Anthurium* had smaller spathes than inflorescences of plants of the cultivar Cherry Red.

In side-by-side comparisons conducted by the Inventors in Apopka, Fla., plants of the new *Anthurium* differed from plants of the male parent, the cultivar Y-14, in the following characteristics:

1. Plants of the new *Anthurium* grew faster than plants of the cultivar Y-14.

2. Plants of the new *Anthurium* were more compact than plants of the cultivar Y-14.
3. Plants of the new *Anthurium* were more freely-branching than plants of the cultivar Y-14.
4. Plants of the new *Anthurium* had smaller leaves than plants of the cultivar Y-14.
5. Plants of the new *Anthurium* and the cultivar Y-14 differed in leaf coloration.
6. Plants of the new *Anthurium* were more freely and earlier flowering than plants of the cultivar Y-14.
7. Inflorescences of plants of the new *Anthurium* had smaller spathes than inflorescences of plants of the cultivar Y-14.

Plants of the new *Anthurium* can be compared to plants of the cultivar Small Talk, not patented. In side-by-side comparisons conducted in Apopka, Fla., plants of the new *Anthurium* differed from plants of the *Anthurium* cultivar Small Talk in the following characteristics:

1. Plants of the new *Anthurium* grew faster than plants of the cultivar Small Talk.
2. Plants of the new *Anthurium* were more freely branching than plants of the cultivar Small Talk.
3. Plants of the new *Anthurium* were more freely flowering than plants of the cultivar Small Talk.

BRIEF DESCRIPTION OF THE PHOTOGRAPHS

The accompanying colored photographs illustrate the overall appearance of the new *Anthurium,* showing the colors as true as it is reasonably possible to obtain in colored reproductions of this type. Colors in the photographs may differ slightly from the color values cited in the detailed botanical description which accurately describe the colors of the new *Anthurium.*

The photograph on the first sheet comprises a side perspective view of a typical plant of 'TWYAN0015' grown in a container.

The photograph on the second page is a close-up view of typical inflorescences of 'TWYAN0015'.

DETAILED BOTANICAL DESCRIPTION

The cultivar TWYAN0015 has not been observed under all possible environmental conditions. The phenotype may vary somewhat with variations in environment such as temperature and light intensity without, however, any variance in genotype.

The following observations and measurements describe plants of the new *Anthurium* that were grown in 20-cm containers, in Apopka, Fla., in a polypropylene-covered shadehouse with light levels ranged from about 1,500 to 2,500 foot-candles. During the production of the plants, day temperatures were about 23° C. to 32° C. and night temperatures were about 21° C. to 24° C. Plants used for the photographs and description were about 18 months from planting. Color references are made to The Royal Horticultural Society Colour Chart, 2001 Edition, except where general terms of ordinary dictionary significance are used.

Botanical classification: *Anthurium hybrida* cultivar TWYAN0015.

Parentage:

*Female, or seed, parent.*—*Anthurium hybrida* cultivar Cherry Red, disclosed in U.S. Plant Pat. No. 12,315.

*Male, or pollen, parent.*—*Anthurium hybrida* cultivar Y-14, not patented.

Propagation:

*Type.*—By tissue culture.

*Time to initiate roots, summer.*—About one to two weeks at 27° C. to 34° C.

*Time to initiate roots, winter.*—About two to three weeks at 21° C. to 27° C.

*Time to produce a rooted plant roots, summer.*—About 12 weeks at 27° C. to 34° C.

*Time to produce a rooted plant roots, winter.*—About 15 weeks at 21° C. to 27° C.

*Root description.*—Thick, fleshy; white in color.

*Rooting habit.*—Moderate branching.

Plant description:

*Plant form.*—Upright with outwardly pointed leaves, plants become outwardly arching as leaves develop; inverted triangle; compact, symmetrical and uniform plant habit.

*Vigor/growth rate.*—Moderately vigorous; relatively rapid growth rate. Plant size appropriate for 10 to 20-cm containers.

*Growth habit.*—Freely clumping habit; plants typically produce about 18 offshoots per plant; full, dense and bushy appearance.

*Plant height, soil level to top of foliar plane.*—About 38 cm.

*Plant height, soil level to top of inflorescences.*—About 38 cm.

*Plant width (spread).*—About 65 cm.

*Stem description.*—Length: About 11 cm. Diameter: About 9 mm. Internode length: About 1.3 cm. Aspect: Upright. Strength: Sturdy, tough. Color, immature: 145A. Color, mature: 146D. Cataphylls: Length: About 5.7 cm. Width: About 2 cm. Shape: Lanceolate. Apex: Apiculate to acute. Base: Clasping. Margin: Entire. Texture, upper and lower surfaces: Smooth, glabrous. Color, when developing, upper and lower surfaces: 146C. Color, fully developed, upper and lower surfaces: 165A.

*Foliage description.*—Arrangement: Alternate; single. Length: About 14 cm. Width: About 8 cm. Shape: Ovate to deltoid. Apex: Acuminate. Base: Truncate. Margin: Entire; with some undulation; leaf upwards longitudinally. Texture, upper and lower surfaces: Smooth, glabrous; rugose. Luster: Glossy; with development, less glossy. Veins: Recessed on upper surface and prominent on lower surface. Venation pattern: Pinnate. Color: Developing leaves, upper surface: 146B; lateral veins, 146A; midvein, 146C. Developing leaves, lower surface: 146C; lateral veins, 146B; midvein, lighter than 146D. Fully expanded leaves, upper surface: More green than 147A; lateral veins, similar to lamina; midvein, 146C. Fully expanded leaves, lower surface: 146B; lateral veins, 146A; midvein, lighter than 146C. Petiole: Aspect: Initially upright; when mature, about 40° from vertical; base, clasping. Length: About 20 cm. Diameter, distal: About 2.5 mm. Diameter, proximal: About 7 mm. Color: 146A to 146B. Geniculum length: About 2 cm. Geniculum diameter: About 3 mm. Geniculum color: 146A to 146B. Wing length: About 2.3 cm. Wing diameter: About 5 mm. Wing color: 146A to 146B.

Inflorescence description:

*Inflorescence arrangement/quantity.*—Spathes with spadices positioned at or just slightly above the foliar plane; inflorescences arise from leaf axils; freely flowering, about 15 inflorescences per plant.

*Time to flower.*—Inflorescences develop year-round in Apopka, Fla.; flowering continuous with about three to four inflorescences developing about every two weeks.

*Inflorescence longevity.*—About four weeks on the plant; about 10 days as a cut flower; inflorescences not persistent.

*Fragrance.*—None detected.

*Spathe.*—Length: About 6.5 cm. Width: About 4.8 cm. Shape: Ovate. Apex: Acuminate. Base: Obtuse to acute. Margin: Entire with some undulation. Texture, upper and lower surfaces: Smooth, glabrous; somewhat rugose. Aspect: Horizontal to folded downward. Color: When developing, front surface: 45A; towards the base, tinged with 147B. When developing, rear surface: 45B to 45C; towards the base, tinged with 147B. Fully developed, front surface: 45B; towards the base, tinged with 147B; with development, color becoming closer to 45C to 45D. Fully developed, rear surface: 46C to 46D; with development, color becoming closer to 51D with 145C at the base.

*Spadix.*—Length: About 3.2 cm. Diameter: About 5 mm. Shape: Columnar, cylindrical; apex, bluntly rounded. Aspect: Mostly upright to slightly tilted outwardly. Color, immature: 8B. Color, mature: 11D; towards the apex, 20A to 20B. Flower appearance: Bisexual, reduced, minuscule. Quantity of flowers per spadix: About 175. Flower diameter: About 1.5 mm. Flower depth: About 2.2 mm. Flower shape: Roughly pyramidal. Quantity of anthers per flower: About eight. Anther color: 155D. Pollen: Sparse. Pollen color: 155D. Stigma color: 155D. Ovary color: 155B.

*Peduncles.*—Length: About 27 cm. Diameter: About 2.5 mm. Aspect: Upright to leaning slightly outwardly. Strength: Sturdy; flexible. Color: 146B to 146C.

*Pedicels* (*stipe*).—Length: Less than 1 mm. Diameter: About 4 mm. Aspect: Upright to slightly leaning outwardly. Strength: Sturdy; flexible. Color: 46B to 46C.

*Fruits.*—Type: Berry. Quantity per spadix: About 100. Length: About 5 mm. Diameter: About 3.5 mm. Texture: Smooth, glabrous. Color, immature: 147B. Color, mature: 16C.

*Seeds.*—Quantity per fruit: About one or two. Length: About 3.5 mm. Diameter: About 2 mm. Texture: Smooth, glabrous. Color: 150D.

Disease/pest resistance: Plants of the new *Anthurium* have not been observed to be resistant to pathogens and pests common to *Anthurium.*

Weather tolerance: Plants of the new *Anthurium* have been observed to be tolerant to wind, rain and temperatures ranging from about 13° C. to 40° C.

It is claimed:

1. A new and distinct cultivar of *Anthurium* plant named 'TWYAN0015', as illustrated and described.

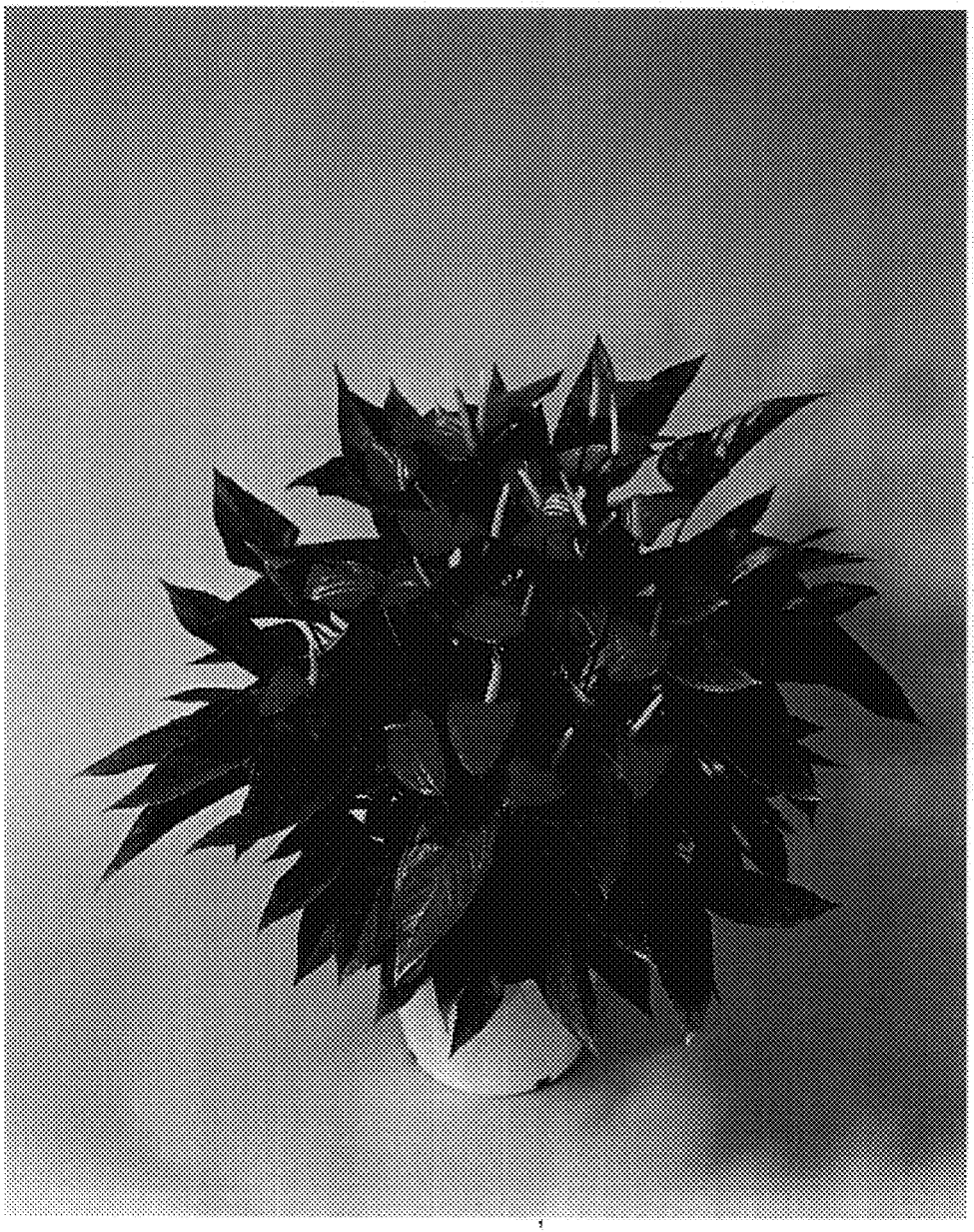

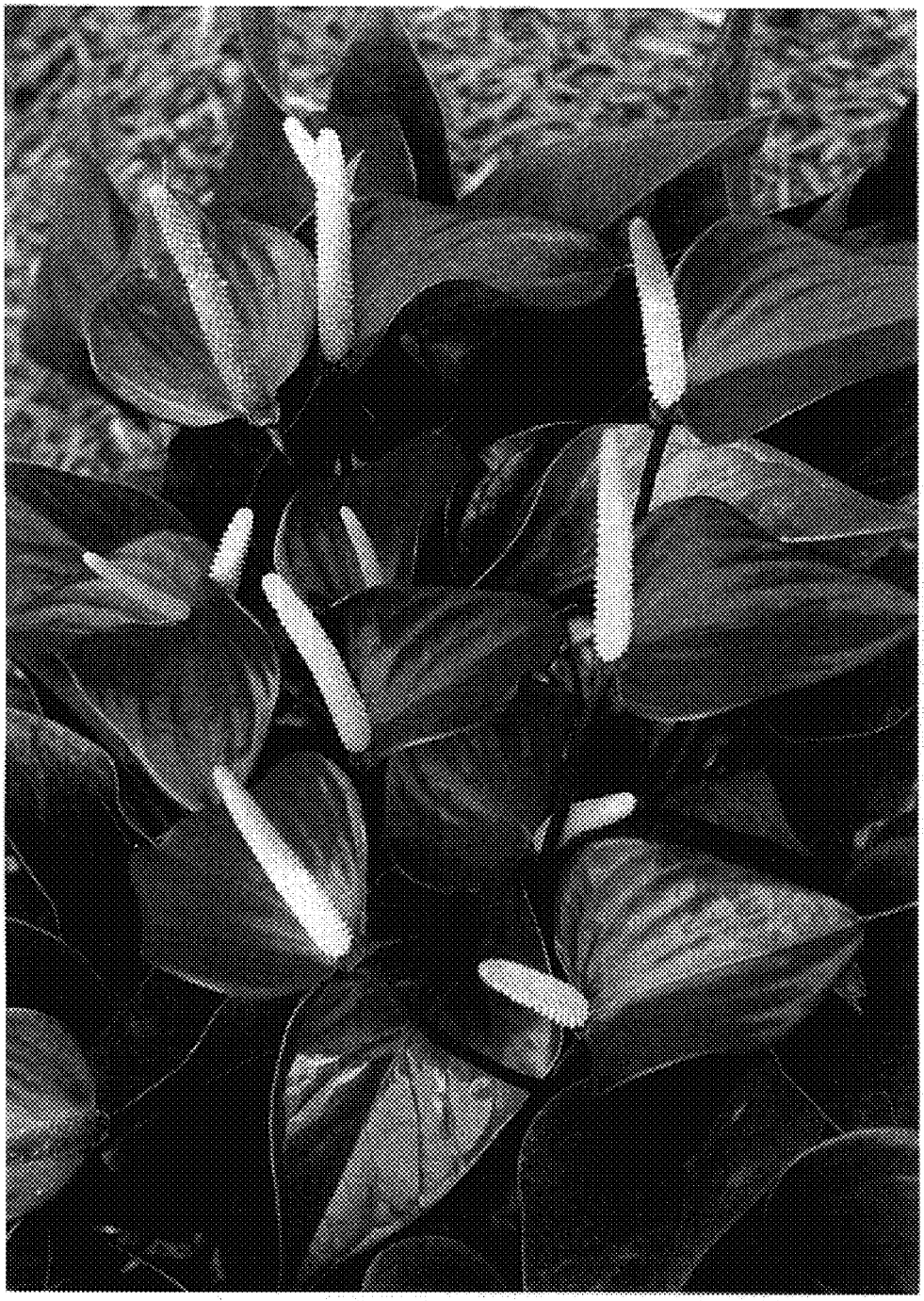

* * * * *